United States Patent
Andersson et al.

[11] Patent Number: 5,880,962
[45] Date of Patent: *Mar. 9, 1999

[54] COMPUTER AIDED PROCESSING OF THREE-DIMENSIONAL OBJECT AND APPARATUS THEREOF

[75] Inventors: Matts Andersson, Lerum; Anders Törnquist, Göteborg, both of Sweden

[73] Assignee: Nobel Biocare AB, Göteborg, Sweden

[ * ] Notice: The term of this patent shall not extend beyond the expiration date of Pat. No. 5,587,912.

[21] Appl. No.: 760,161

[22] Filed: Dec. 3, 1996

Related U.S. Application Data

[62] Division of Ser. No. 271,457, Jul. 7, 1994, Pat. No. 5,587,912.

[30] Foreign Application Priority Data

Jul. 12, 1993 [SE] Sweden .................................. 9302399

[51] Int. Cl.⁶ .................................................. G06F 19/00
[52] U.S. Cl. ............................. 364/468.04; 364/468.25; 364/474.05; 433/215; 623/901
[58] Field of Search .................... 364/468.04, 474.01, 364/474.05, 474.22–474.24, 468.24–468.26; 433/204, 213, 214, 223; 623/901

[56] References Cited

U.S. PATENT DOCUMENTS

5,184,306  2/1993  Erdman et al. .................... 364/474.24
5,266,030  11/1993  Van Der Zel ........................... 433/214
5,587,912  12/1996  Andersson et al. ................ 364/468.04

Primary Examiner—Paul P. Gordon
Assistant Examiner—Steven R. Garland
Attorney, Agent, or Firm—Pollock, Vande Sande & Amernick

[57] ABSTRACT

A process for generating data for manufacturing a three-dimensional body utilizing a computer-aided design program. Mathematical models corresponding to reference three-dimensional bodies are provided. The mathematical models are stored in a memory of a computer. Input data representing an input three-dimensional body are provided to the computer. A representation the input data is generated on a display of the computer. The representation includes at least a portion of a contour of a vertical section extending through a central axis of the input three-dimensional body. A location of a preparation line is determined on the representation of the input three-dimensional body. A representation including at least a portion of a contour of a vertical section extending through a central axis of the one of the mathematical models is generated on the display of the computer superimposed on the representation of the input data. A modification of the input data is generated on the display of the computer utilizing an input device of the computer based upon a comparison of the representation of the input three-dimensional body with the representation of the mathematical model. The output data representing the modified input three-dimensional body is generated. The output data is transmittable from the computer for manufacturing the three-dimensional body.

29 Claims, 3 Drawing Sheets

COMPUTER AIDED PROCESSING OF THREE-DIMENSIONAL OBJECT AND APPARATUS THEREOF

This application is a Divisional of U.S. patent application Ser. No. 08/271,457, filed Jul. 7, 1994 now U.S. Pat. No. 5,587,912.

FIELD OF THE INVENTION

The present invention relates to a process for achieving, by means of input data representing a three-dimensional body usable in the human body, output data which can be used for manufacturing purposes and represents an altered or extended variant of the three-dimensional body. Example of such three-dimensional body are a tooth sleeve, dental bridge or other dental structure. The input data are fed to a computer from which the output data can be extracted based upon the input data. The computer exhibits a computer screen and operates with a CADD-program (Computer Aided Dental Design). The program relates to CAD-programs (Computer Aided Design) and has been adapted for the functions and fields of the present application. With the aid of the program, an alteration or extension attributable to the body variant relative to the three-dimensional body can be simulated. Also included are input devices, by means of which the alteration or extension in question is effected. The invention relates also to a device for realizing the above process.

BACKGROUND OF THE INVENTION

From the Swedish patent 9003967-8 (468 198), it is previously known to utilize computer-aided manufacturing of dental and other products usable in the human body. The known equipment proposes purely general usage of computer-aided equipment, in which particular alterations and extensions can be attached to a model, in question or to fed-in data representing a model and design measures relating to the product in question can be taken with the aid of attached input data.

In the case of conventional manual formulation of tooth sleeves, tooth crowns, and the like, the dentist/dental technician prepared the model which was dispatched to the manufacturer. When the dentist/dental technician received the model back, adjustments were made to it and sent back to the manufacturer, until a product with approved results was obtained.

Readings of three-dimensional bodies normally involve large quantities of data. Various measures have been proposed for keeping these data quantities down.

SUMMARY OF THE INVENTION

There is a need to be able to formulate more exact models for the practice of the dentist/dental technician. The object of the present invention is to solve these problems and to propose a tool for highly advanced, on-site model production or model copying.

There is also a need for the model to remain at the practice in order to be used privately and to avoid dispatching of the model or its equivalent to the manufacturer by mail, courier, etc. The invention solves this problem permitting sending of only data relating to the shaping of the model to the manufacturer via modem, diskette, and the like.

The present invention proposes the utilization of computer-aided equipment, which is normally a new instrument for currently practising dentists/dental technicians. It is therefore important that the tools or aids should be operated by simple handling principles and routines. The present invention also solves these problems.

The manufacturing accuracy in products of this type must be kept high, for example $\pm 10\,\mu m$, in order to function well when fitted to a patient. Such accuracy can entail machine accuracies and computing accuracies of $\pm 0.0015$ mm. The design or formulation of tooth sleeves, dental bridges, etc., must therefore be carried out with great precision and clarity. The output data which is produced and which will serve as a basis for milling and other machining coordinates must be accurate. The invention also eliminates this problem.

In this type of computer-aided design, certain features are included which can be practiced and realized only by dentally skilled staff who will be able to apply their professional expertise in the model formulation phase. The latter must be effected without any complicated handling procedures and equipment. Present invention solves this problem.

There is a need to minimize the contributions made by the dentist/dental technician in connection with the formulation of tooth sleeves, dental bridges, and the like present. The invention largely solves this problem and permits routines in which repeated dealings with the product can be eliminated. The dentist/dental technician can make a clear contribution and does not need to proceed in successive stages. The dentist/dental technician can easily modify the shape in the copying process, as well as when checking patient-matching and can optimally utilize available spaces for cement and modifications. Accurate adjustments can be made to the interface between the sleeve/bridge and tooth remnants, jawbone, and the like.

In connection with computer-aided copying of a dental product, it has been shown that the identification of the preparation line on the computer screen runs up against problems. The invention solves this problem and offers aids to enable the dentist/dental technician to fix the preparation line for the output data with great accuracy.

In the formulation of models and products in the form of tooth sleeves, it is essential and crucial to the entire production that the angling of the sleeve material at the preparation line (the end edge of the shell) or preparation boundary be made exact. The angling should be effected based upon the position on the tooth, that is a first angle should be obtained on the outer side of the tooth and a second angle on the inner side of the tooth, and the like. This applies also to the bulges of the tooth/model on the inner and outer sides, etc. The invention solves this problem and proposes the utilization of macro models (with algorithms/rules) for various basic forms of teeth. The macro models affect upon the respective model copying, i.e. if the product in question relates to the use of a certain type of tooth, the macro model of this tooth is applied to the product in question.

Shapes of the teeth also vary within broad limits. Special characteristic features can nevertheless be traced in the different basic forms, namely eye-tooth, front tooth, milk tooth, and the like. According to the inventive concept, the special characteristic features should be documented and utilized in the copying and production of the respective product. The present invention solves this problem and proposes utilization of a library in which characteristics of basic forms are stored in the ongoing copying and manufacturing production. As produced products are tested on and used by patients, experiences based thereon can be fed back to the system and the characteristics gradually perfected. The system can also be made self-teaching insofar as it accepts only the optimal product in overall terms.

Teeth, models, and the like are largely individual and scanning of three-dimensional bodies of this type normally requires large data quantities to be handled. There is a need to reduce these data quantities but nevertheless achieve the sought-after precision in copying and production of the products in question. The present invention solves this problem and enables the copying and manufacturing period to be reduced using the same compared computing power. From the software viewpoint, the preparation time for milling coordinates of a sleeve, for example, can be realized according to the invention in as short a time as about 50 sec. using a computing power which is found in conventional personal computers currently sold on the market.

In the process according to the present invention, one its characteristics is that the input data is read and stored by the computer into memory cells and that the program is directed, by means of first signals generated by one or more first activations of the input devices, to generate, with the aid of the input data, representations of the surface of the body in the form of contours of a number of vertical sections extending through the center axis of the body. The contours are here presented one at a time on the screen. The process is also characterized in that the CADD-program is directed, by means of second signals generated by one or more second activations of the input devices, to simulate on the cross-sections/contours modification, for example, alteration or extension attributable to the body variant. The process is finally characterized in that the program is directed, by means of third signals generated by one or more third activations of the input devices, to store in memory cells data attributable to the body variant simulated by means of the altered or extended vertical sections. This data is utilized to generate the output data.

In one embodiment, the input data is related to information acquired from a system of coordinates in which the body is installed. The system of coordinates in question requires two predictably movable parameters and one unpredictably variable parameter. This system of coordinates is utilized throughout the manufacturing system, i.e. in the reading function, the copying function and the manufacturing function. The input data is located in one or more first data files and, following copying by means of the computer, the output data is located in one or more second data files having the same or equivalent format as the respective first data file. In the event of alteration or extension to a cross-section/contour which is controlled by means of the second signals, an action takes place according to a control system which is utilized by the program and relates to one or more factors. Examples of such factors can be tooth type, front and rear of the tooth in question, the height of the respective tooth, bulging or bulges of the respective tooth, angle/angles at the preparation line, etc.

In a further embodiment, the CADD-program is directed, by means of fourth signals generated by one or more fourth activations of the input devices, to represent a displaceable horizontal line which, based upon the fourth activation, is controllable in the vertical direction of the vertical sections/contours. Upon displacement of the horizontal line to a part of the respective vertical section or contour representing the preparation line of the body, a line, represented by dots, is generated by the program and presented on the screen. The latter line therefore represents the preparation line of the body when the three-dimensional body is spread out on a flat surface. Data relating to the preparation line representation, forms part of the output data.

In one embodiment, a library is utilized for saving data files and macro models attributable to various basic types of teeth, for example eye-tooth, front tooth, milk tooth and the like. Data in the data files is utilized in copying each subsequent model or equivalent. Use is made of the knowledge, acquired by experience, of whether previous creations or copyings have satisfied the requirements or not. Comparison-making members are actuated or activated to conduct a comparison between a body variant currently under formation and previously made body variants. The library function can be performed using a register utilizing a self-teaching function from which the dental technician receives help in his product formation. Optimal shapes for the various tooth types are implemented in the equipment and the total number of body variants created in the equipment can be utilized, as well as any experience-based information supplied by practising dentists/dental technicians. A number of macro models can further be utilized. The macro models are attributable to rules and mathematics linked to various basic functions in the copying and production. Basic functions of this type can be the basic forms of the teeth, the creation of a base surface, consideration of the tooth type, formulation of vertical and circular sections/contours of the respective body variant/tooth, alteration of the height of the tooth in various vertical sections, bulging of the inner and outer sides of the tooth, thickness of a utilized tooth sleeve, and the like.

In one embodiment, the equipment is utilized for the formation of tooth sleeves. By means of fifth signals generated by one or more fifth activations of the input devices, an item with shell-thickness information is attached to a respective vertical section or contour, so that a shell is presented on the screen based on the respective vertical section/contour. With sixth signals generated by sixth activations of the input devices, the connection angles of the respective vertical section of the shell can also be modified. The connection angle is situated at the preparation line and relates to the shaping of the connecting surface/connecting lip against a tooth remnant, mouth cavity, jaw and the like.

A device exhibiting the special characteristic feature of the invention is principally characterized in that it forms a station which can be set up at the practice of a dentist/dental technician or equivalent professional and by means of which the body variant can be simulated by means of a CADD-program or CADD-function formulated for the purpose. The station here comprises memory storage cells for the input data. The CADD-function is arranged so as to reproduce the surface of the body on the screen and to permit an alteration or extension of the latter according to the body variant to operate with a number of vertical sections, extending through the central axis of the body, of the body contour or body variant contour. There is therefore a two-dimensional representation of the read or manufacturable three-dimensional body. The vertical sections (the two-dimensional representations) can be represented on the screen one at a time, and attachable alterations or extensions related to the alteration or extension of the body, variant relative to the body can also be formulated on the screen. Memory cells, which can be constituted by the above memory cells or by additional memory cells, are arranged to receive and store data attributable to the altered or extended vertical sections/contours, which data form or serve as a basis for the output data.

By virtue of the above, an effectively functioning tool or aid is obtained for the practice of a dentist/dental technician or equivalent person within a different professional category for treatment of the human body. The copying function can be performed with great precision and saves time for the dentist/dental technician, who is able to simplify his/her routines in the production of dental products. Although the station in question is separated from the manufacturing site, the high accuracy can be maintained throughout the system. The handling of the equipment does not require a higher degree of specialization among the staff involved. This should be contrasted with the staff at a general CAD-station, for example an auto-CAD station, which has to be operated by experts. The two-dimensional representation allows substantial interaction between users and the computer unit. The work which is done by the dental technician remains in the office, and more complicated shapes and preparations can be managed. Control over manufacture can be obtained at an early stage on the screen. Follow-up work is reduced or eliminated completely.

BRIEF DESCRIPTION OF THE DRAWINGS

A presently proposed embodiment of a process and a device according to the invention will be described below with simultaneous reference to appended drawings, in which.

DETAILED DESCRIPTION OF THE PREFERRED EMBODIMENT

Figure 1:
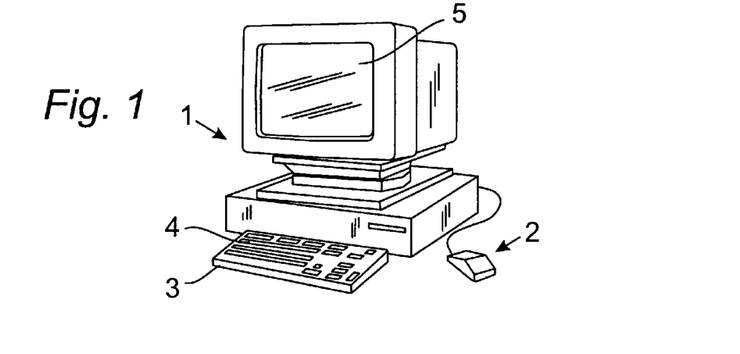
FIG. 1 shows a personal computer which can be used for the copying function

In FIG. 1, a computer unit 1 is denoted by 1. The computer unit 1 can comprise a personal computer, e.g. an IBM-compatible personal computer having a type 386 or type 486 processor. The operating system can be comprise DOS 5.0 type or higher and the internal memory capacity should be at least 2 MB. The computer can expediently be provided with a "mouse" function 2. A keyboard terminal 3 having terminal keys 4 should additionally be included. The computer 1 is preferably provided with a color screen 5 and can have an extra I/O card, as it is known. In addition, the computer can comprise a modem which can be integrated in the computer or can constitute a separate unit. The modem is preferably Hayes-compatible and is arranged so as to communicate with a manufacturer via the telecommunications network (the public telecommunications network). For the communications, standard programs can be used, e.g. a Commute 2.0 program from Central Point, which are included with the software.

The computer unit 1 also operates with a CADD-program which is built on the same principles as conventional CAD-programs, but has been adapted and perfected for dental copying and production. The adaptation of standard CAD-functions has been carried out as described below.

Figure 2:
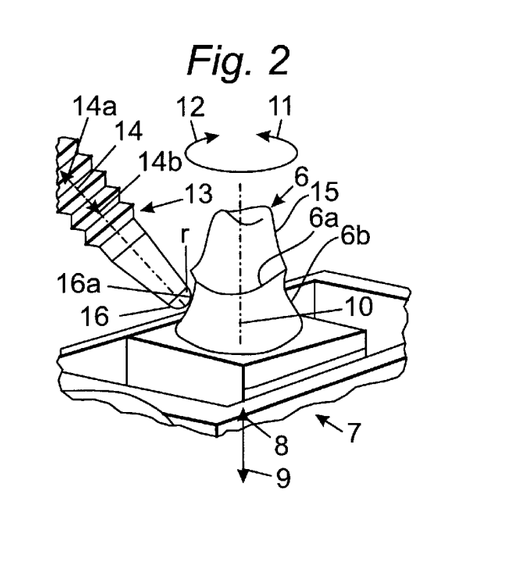
FIG. 2 shows the installation of the model in a system of coordinates and a scanning function for the generation of input data

In FIG. 2, a model prepared by a dentist/dental technician is denoted by 6. The model is aligned in a fixture 7. The fixture 7, in turn, is disposed on or in a rotary holder, which can additionally be raised and lowered in the directions of the arrows 8 and 9, these coinciding with the direction of the central axis 10 of the model 6. The model 6 is rotated around the central axis 10 in the directions of the arrows 11 and 12. The model 6 is turned and vertically displaced, therefore, relative to a scanning device 13, which is longitudinally displaceable along its central line 14, but is otherwise fixedly disposed relative to the rotating, rising or descending model 6. The model 6 is rotated, during scanning, at 40–100, preferably 50–70 revolutions per minute. The rise for the vertical movement of the model 6 during the rotation can be 0.1–0.4 mm per revolution. The scanning device 13 therefore comes to track the contour 15 of the model 6. The scanning device 13 exhibits a spherical front surface or probe 16, which is physically brought to bear against the surface in the present case. The scanning device 13 operates with great precision with respect to the scanning function. The body is scanned, for example, 360 times per revolution, i.e. scanning takes place at each degree of turn.

Figure 3:
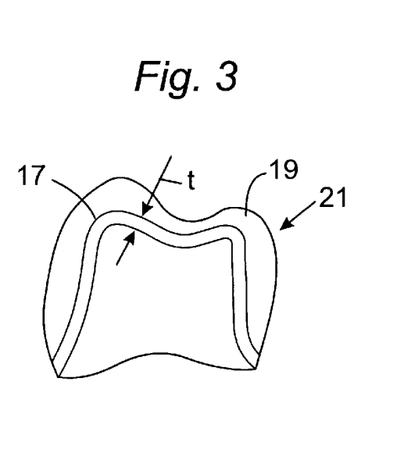
FIGS. 3–4 show examples of various shapings of a copied product, in vertical section.
Figure 4:
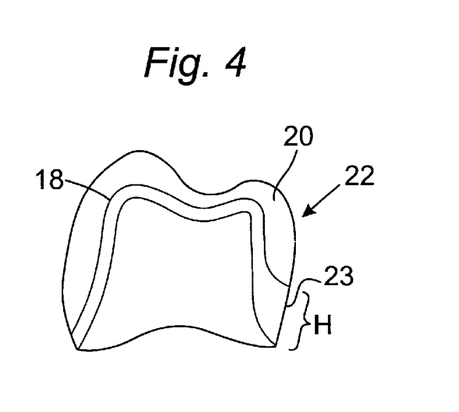

In accordance with FIGS. 3 and 4, differently shaped tooth sleeves 17 and 18, respectively, will be copied or produced, based on the scanning according to FIG. 2. The CADD-function in the computer 1 can represent and reproduce contours or vertical sections of the acquired input data from the scanning according to FIG. 2. To the shown contour, a shell thickness t can be applied, which will be valid for the sleeves 17 and 18. The sleeves 17 and 18 will constitute a building block for a utilized tooth material 19 and 20 respectively, e.g. in the form of plastic, titanium, ceramic, etc. The formulation facility on the screen enables the dental technician/dentist to experiment with a visual model and "construct" an optimal tooth 21 and 22 respectively. In comparing the FIGS. 3 and 4, it is apparent that the thickness can be given different variations along the extents of the shell 17 and 18, respectively, in the peripheral direction and/or vertical direction(s). The shell 18 according to FIG. 4 thus contains a thickness 23, which is not shown in the embodiment according to FIG. 3. The thickness of the shell can further be varied around the periphery of the model or copy, and the height H of the thickness 23 according to FIG. 4 can thus be varied around the periphery, etc.

Figure 5:
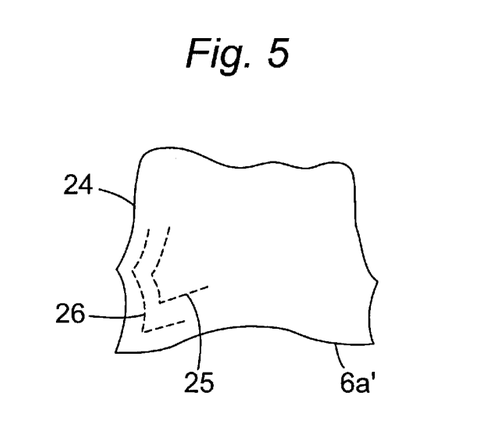
FIG. 5 shows a contour of a model during copying and the effect produced during the copying, in vertical section.

The CADD-programs represent vertical sections one by one in accordance with FIG. 5, which shows a vertical section or contour 24 extending through the central axis 10 according to FIG. 2. In known fashion, the contour 24 can be varied in size, as shown by contours 25 and 26. The surface of the model 6 (see FIG. 2) can thus be represented on the screen by the depiction of, for example, 360 vertical sections/contours through the central axis 10. The terminal key 4 according to FIG. 1 can be actuated to show the vertical sections one by one on the screen and to advance the various vertical sections or contours in a specified on non specific order.

Figure 6:
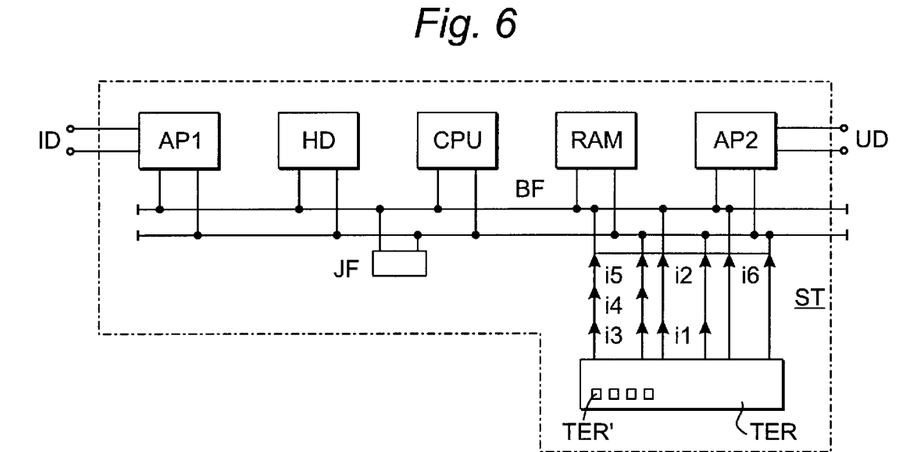
FIGS. 6–7 show examples of the functional structure of the computer unit, in a /block diagram form.
Figure 7:
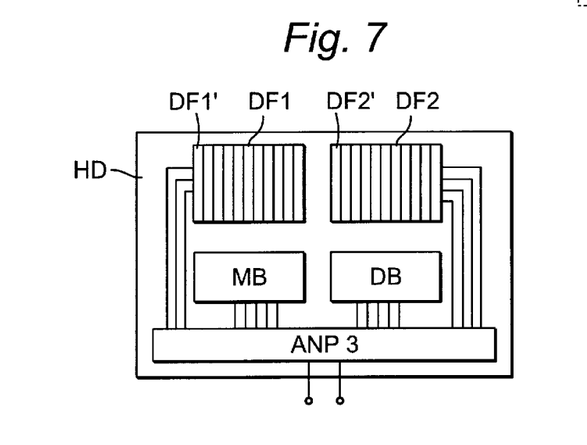

FIGS. 6 and 7 show examples of the internal structure of the computer unit 1. This comprises a CPU of the above-specified type.

A RAM memory and a hard disk HD are additionally included. The equipment forms a station which can be set up at the place of work of the dentist/dental technician and which can possibly be coordinated with a reading function (not specifically shown here) of models (preparation models). The station has the designation ST. Also forming part of the computer installation is the abovementioned terminal TER. Matching circuits AP1 and AP2 are also included. Via the matching circuit AP1, input data ID is received according to the above. Via the matching unit AP2, output data UD can be transmitted.

According to FIG. 7, the hard disk HD in accordance with FIG. 6 comprises memory space DF1 and DF2 for data files for input and output data respectively. Additionally included are a macro model library MB and a data file library DB. The hard disk HD comprises a matching circuit ANP3, which connects the hard disk HD by a bus connection BF to other units mentioned above. Also included is a comparison-making member JF, which is described in more detail below. The bus connection can be arranged for 32 or 64 bits. In order to raise the speed of the equipment, the RAM-memory is utilized at full capacity.

The input data ID is received and stored in a first file DF1' and the data, output data UD, to be transmitted from the equipment is located in a second data file DF2'. The various files have an equivalent format.

A number of signals generated by means of the actuating members (input devices) TER' on the terminal TER are shown in FIG. 6. The terminal TER has three parallel connections to the bus to offer an illustration of the signals. By means of first signals i1 generated by one or more first activations of the devices TER', the CADD-program is directed to generate, with the aid of the input data in the data file DF1', representations of the surface of the body in the form of contours of a number of vertical sections extending through the central axis of the body, see FIG. 5. By means of second signals i2 generated by one or more second activations of the input devices, the program is actuated to simulate on the cross-sections/contours an alteration or extension comparable to the body variant, see FIGS. 3, 4 and 12. By means of third signals i3 generated by one or more third activations of the input devices, the program is directed to store in memory cells DF2 data attributable to that body variant simulated by means of the altered or built-on vertical sections. The data can form or serve as a basis for the output data. By means of fourth signals generated by one or more fourth activations of the input devices, the program is directed to represent a horizontal line, see FIGS. 8, 9 and 10, which, in response the fourth activations, is controllable in the vertical direction of the vertical sections, as described below. By means of fifth signals i5 and sixth signals i6, the program is directed to attach to a respective vertical section or contour an item of shell-thickness information, so that a shell is presented on the screen for a respective vertical section/contour, see FIG. 12, or to actuate a connection angle on a respective vertical section, see FIGS. 13–15.

The hard disk also comprises storage spaces or a library for saving macro models and data files which are attributable to different basic types of preparations and teeth, e.g. eye-tooth, front tooth, etc. According to the above, saved information serves as a basis for future creations of subsequent simulations and body variant formations. Characteristic information is stored and can be modified by acquired experiences of how patients feel about produced products. Information is fed back to the system, for example via the terminal TER, by practising dental technicians/dentists, scientists, etc. The library can be configured to have a self-learning function of a type which is known meaning that the characteristics are constantly being perfected. The characteristics are applied to a respective model, tooth, and the like currently undergoing copying and model formulation. The preparation boundary on the model can therefore be adapted to the respective tooth type, as well as bulges, heights, extents in the horizontal direction, and the like. The implementation can be effected in a manner which is known, using program-based measures.

Figure 8:
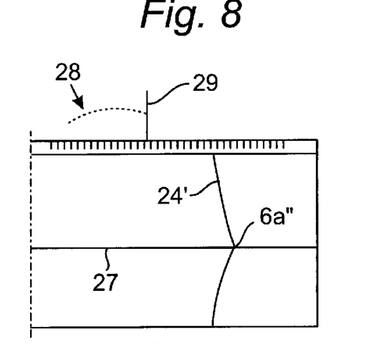
FIGS. 8–10 show the fixing of the preparation line on a model, in diagram form.
Figure 9:
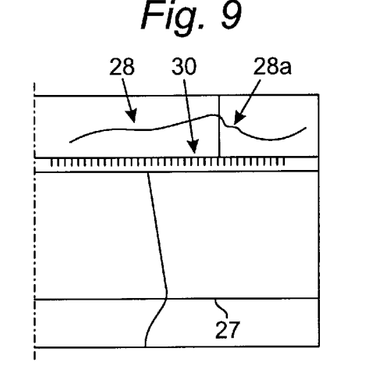
Figure 10:
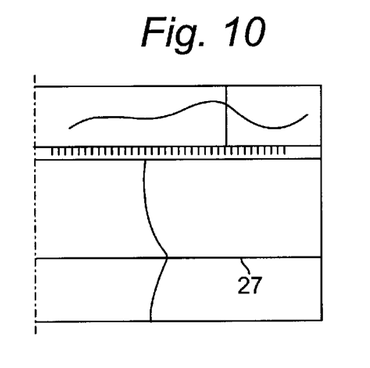

In FIGS. 2 and 5, a preparation line 6a and 6a' respectively is indicated on the model. The model should be configured such that the preparation line remains clear, which can be realized by means of the arrangement of a recess or indentation 6b below the preparation line. The fixing of the preparation line is a special skill which is practiced by the dental technician/dentist. In order to incorporate data relating to the preparation line into the output data from the computer installation, the process according to FIGS. 8, 9 and 10 is utilized. A horizontal line 27 is arranged such that it is displaceable in the vertical direction of the screen by means of the input devices and the CADD-program. FIGS. 8, 9 and 10 show various vertical positions of the horizontal line. In the figures, the contour 24' has additionally been enlarged in connection with the position of the preparation line or preparation boundary 6a''. The line is installed with the aid of the input devices (keys, mouse, recording members and similar members), so that it intersects the preparation line or boundary 6a'' in the section according to FIG. 8. A line 28 represents the preparation line on the various vertical sections or contours. A vertical line 29 shows the position of the vertical section relative to the line. Each section can be represented, in the line 28, by a dot, and it can be seen from FIG. 8 that a number of vertical sections have been represented by a number of dots. The representation of the preparation line according to the vertical section in FIG. 8 will thus be positioned at the line 29, which can therefore be realized with the aid of the input devices, etc. FIGS. 9 and 10 show other sections, and the line 28 shows how the fixing of the preparation line has progressed.

In greater detail, the process proceeds with the operator starting from the main menu in the user program. The data file is marked by the use of a band of light at the top of the screen. "CADD" is selected from the main menu and, by further actuation of the keys, the data file can be installed in the working memory. The CADD-program is started up and the preparation model is represented, according to FIG. 5, on the screen. The image is enlarged in accordance with FIGS. 8, 9 and 10. The horizontal line can be adjusted on the profiled edge 6a'', where the dental technician or dentist determines from experience where the preparation line goes. The markings are realized with the line 28. After this, the computer accomplishes the formulation of a subsequent profile, etc. The number of scannings in a respective revolution can total, for example, 36, i.e. every tenth degree. The curve between the dots is interpolated in known fashion, for example Lagranges/interpolation formula, Cubic's spine, etc. Following the formulation of the complete line 28, assessments can be made of whether the line correctly reproduces the preparation line. The latter should assume a uniformly soft shaping without any sharp portions or edges. If FIG. 9 is considered, for example, it can be seen that at 28a there is a sharp deviation. This should probably be rectified. This can be realized by reformulating the vertical section on the screen and making a new estimate of the preparation line with respect the particular vertical section. The scale 30 can be utilized together with the vertical line 29.

In accordance with the above, the preparation model is rotated slowly while scanning proceeds by the scanning unit, so that the surface of the model is read along a spiral-shaped line which starts below the preparation line and ends directly above the model. The normal-sized tooth/model which is thus described can be described by a data quantity comprising about 20,000 measurements, which is regarded as a relatively small quantity and allows effective handling of the copying. The data program transforms the measuring points into a surface, which is converted into a large quantity of vertical sections or contours. The profile of the preparation model can thereby be studied from all angles. The alterations and extensions to the various vertical sections form the basis for the copying function.

The macro models are utilized as described below. A macro is herein constituted by a macro model plus parameter information relating to the shell or sleeve shaping, the angle at the edge or lip of the shell or sleeve, the vertical position of the supporting edge of the shell or sleeve on the tooth remnant, and the like. The respective macro model constitutes a mathematical model which can be integrated or superimposed on the visual display unit with, for example, information (graphs) attributable to the shell/shape of the shell. The respective macro model is attributable to a tooth type (for example milk tooth, eye-tooth, and the like), preparation form, and the like. The respective macro model is stored in an assigned data file which is filed in a library from which the macro models can be selected by means of input devices, in a manner which is known, by means of the command (the macro name is entered by means of the input devices in known fashion. Icons, too, can be utilized for this function). Correspondingly, different files for read data and calculated data can be arranged for different tooth shapes, preparation shapes, and the like. The files can be run together for forming desired shapes, so-called "unions", on the visual display unit, by means of which unions options are provided on the screen for the formation of simultaneous graphic representations. Read data can here be attributable to inner surfaces, outer surfaces, and the like. Also, bodies and shapes can be formulated for free merging on the screen ("morphing", as it is known). The files can thereby be merged and different parts of the contours mutually exchanged. This process enables an inner surface file and read wax-hood file, for example, to be merged and tied to a macro model. The manual work which is input in this way can be automatically processed, which provides accuracy in difficult preparation cases/shapes. High accuracy of fit can be obtained, and the work can be maintained by virtue of the computer control managed by a dental technician.

The dental technician/dentist is therefore able, in the case involving macro models, to select desired macro models from the library and attach these to graphic representations of shell or sleeve profiles which are formulated on the computer screen. The dental technician/dentist is also able to choose shell thickness and sizes of the preparation angles and thereby create extensions, alterations, adaptations, and the like, in the originally formulated graphic representation of the shell/sleeve. Those shapes of tooth creations which have been worked out in advance and obtained by experience yield major advantages. The advantages relate, among other things, to handling. The interaction between users and the computer can be substantially reduced, for examples when compared with a conventional CAD-function in which the interaction is extensive in the formulation of three-dimensional bodies.

The read data/files can be attributable to the final shape of the tooth and the current shape of the tooth remnant. By running together and superimposing the information, optimal solutions of the shaping of the supporting body, here referred to as "union", can be achieved. The structure of the shell or sleeve can also be adapted according to the properties of the extension material, which material can be constituted by, for example, porcelain. Choice of color can also constitute a parameter in this context. References to the preparation line can also serve as a basis for the structure.

Figure 11:
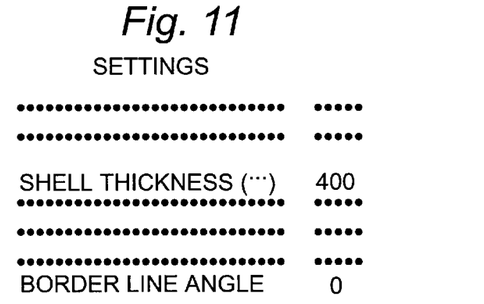
FIG. 11 shows a menu on the computer according to FIG. 1, which menu relates to the application of shell thickness and angle at the preparation line to a contour or a vertical section.
Figure 12:
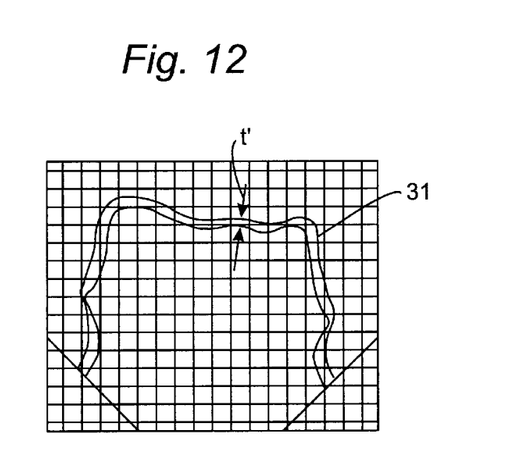
FIG. 12 shows the representation of a shell on the visual display unit, in vertical section.

A copied model according to FIG. 2 can be realized. FIG. 11 shows a menu in which it is possible to construct a shell 31 according to FIG. 12. The menus can therefore comprise "shell thickness" and, by selection of a keyboard option, a desired thickness, for example 400 micrometers (0.4 mm), can be chosen. In FIG. 12, the thickness is indicated by t'. Using the same menu, an angle can also be chosen at which the copy connects with a preparation line, see FIGS. 13, 14 and 15, which represents exhibiting files containing macro model, shell and angle. The latter figures show the angles 0°, 20° and 40° respectively. The angles, thickness and the like are or can be dependent upon tooth type (eye-tooth, milk tooth, and the like). The angles in question can be connected, in copying, to the preparation line and optionally chosen from 0° to 40°, starting from a vertical line. This too is stored as macro models in data files and automatically follows the data file. If an angle other than 0° is desired, this can be marked on the menu according to FIG. 11 by indicating the number of degrees in the angle function. This can be realized in connection with the indication of the shell thickness, which can itself be altered correspondingly.

Figures 13, 14, 15:
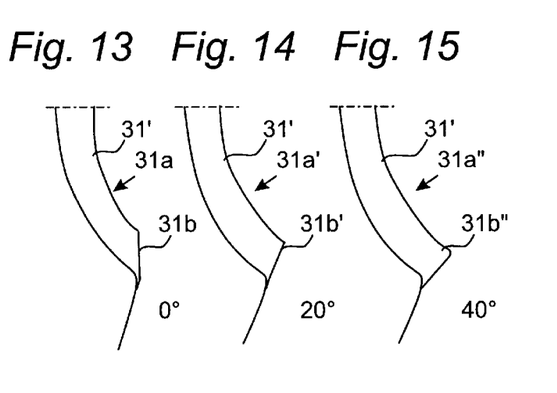
FIGS. 13–15 show three different examples of the angle at the end of the shell in connection with the preparation line.

The angles relate to the angles between the free end surface 31$b$, 31$b'$, 31$b''$ of the shell and a vertical line. The depression 31$a$, 31$a'$, 31$a''$ above the boundary surfaces is dependent upon the angles and can be effected (represented) with the aid of macro models.

Figure 16:
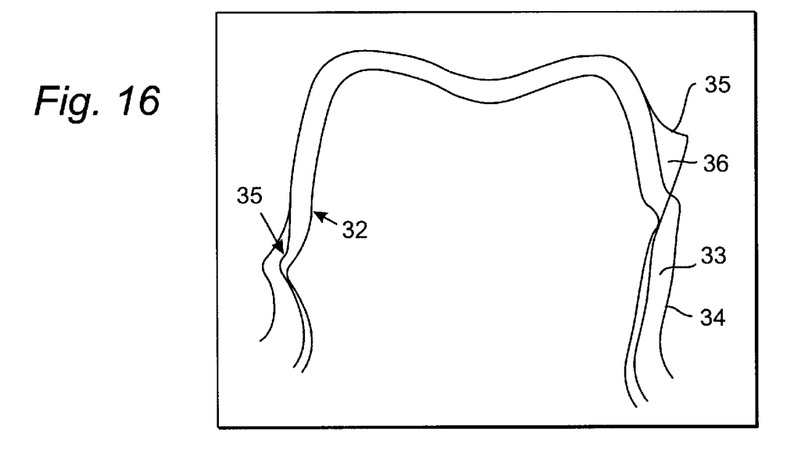
FIG. 16 shows a finished preparation having a macro model represented on the screen, in vertical section.

In FIG. 16, a graphic representation, on the computer screen, of a contour or vertical section of a read surface (inner surface in the representation) is shown by 32. The reading is stored in a first file. On the representation, a shell 33 has been attached, which has been realized using a macro model in the program, which may have been acquired from a second file. The outer surface of the shell has been indicated by 34. The thickness of the shell 33 can be chosen according to the above. In addition, from the macro model library, a macro model representation 35 has been fetched from a third file (by the operator). By formating of different macro models and superimposing this on the shell representation and by working with different shell thicknesses, edge angles at the preparation boundary and/or other parameters such as the defined height of the relief edge on the tooth remnant, the operator (dental technician) is able to effect alterations, adaptations, extensions, and the like to be supplied to the supporting structure (the shell, sleeve, etc.) The adaptation is preferably made with regard to material in the sleeve (e.g. titanium) and the particular extension material 36 (porcelain or other material). Color, appearance, and the like, can here be included as parameters.

Output data according to the above and which constitute the end result of the copying and designing can be located in a data file which is transmitted to the manufacturer. The data files of incoming and outbound data are preferably configured in the same format. According to the above, the outbound data file is dispatched by modem, via the public telecommunications network, according to the above.

A number of basic types of macro models can be utilized in the program in question. A macro model can thus be utilized for the limiting angle function, shell thickness function, edge extent function and edge top function. In addition, the angle function for a recess 6$b$ can be included as a macro model, as are the angle of curvature functions in respect of the preparation line. The system of coordinates (preferably polar) which is utilized jointly for model reading and manufacture operates with two predictably movable or "locked" parameters and an unpredictably variable or non-"locked" parameter. The one of the former parameters is constituted by the rotary movement of the model 6 according to FIG. 2, which is 11 or 12 and can, for example, be constant or vary in a predefined manner. The other predictable or "locked" parameter is constituted, in the case according to FIG. 2, by the constant displacement of the model in the directions 8 or 9, coinciding with the central axis 10. The unpredictable parameter is constituted, in the case according to FIG. 2, by longitudinal displacement movements of the scanning member 13 along the longitudinal axis 14, which are caused by the shaping of the contour 15. A fourth parameter, which is itself predictable, might be the radius of the scanning probe.

The invention is not limited to the embodiment shown by way of example above, but can be subject to modifications within the scope of the subsequent patent claims and the inventive concept.

We claim:

1. A process for generating data for manufacturing a three-dimensional body utilizing a computer-aided design program, said process comprising the steps of:

providing mathematical models corresponding to reference three-dimensional bodies, said mathematical models being stored in a memory of a computer;

providing to the computer input data representing an input three-dimensional body;

generating through the computer-aided design program a representation the input data on a display of the computer, the representation comprising at least a portion of a contour of a vertical section extending through a central axis of the input three-dimensional body;

determining a location of a preparation line on the representation of the input three-dimensional body for manufacturing the manufactured three-dimensional body;

generating through the computer-aided design program a representation comprising at least a portion of a contour of a vertical section extending through a central axis of the one of the mathematical models on the display of the computer superimposed on the representation of the input data;

generating through the computer-aided design program based upon a comparison of the representation of the input three-dimensional body with the representation of the mathematical model a modification of the input data on the display of the computer utilizing an input device of the computer; and generating through the computer-aided design program the output data representing the modified input three-dimensional body, the output data being transmittable from the computer for manufacturing the three-dimensional body.

2. A process according to claim 1, wherein the input data relates to information from a system of coordinates in which the surface of the input three-dimensional body is read and wherein said system of coordinates requires two predictably movable parameters and one unpredictably variable parameter.

3. A process according to claim 1, wherein the input data is stored in a first data file and the output data is stored in a second data file having a format at least equivalent to that of the first data file.

4. A process according to claim 1, wherein when said modification of said input data is performed, an action takes place according to a control system which is utilized by the program and relates to one or more factors.

5. A process according to claim 4, wherein said input three-dimensional body is a tooth and said factors include tooth type, front and rear of the tooth in question, tooth height, bulging, angle at the preparation line, and preparation shapes.

6. A process according to claim 1, further comprising generating through the computer-aided design program upon activation of the input device signals to represent a displaceable unit, which, based upon the signals is controllable in the vertical direction of the vertical sections.

7. A process according to claim 1, wherein the reference three-dimensional bodies represent different types of teeth.

8. A process according to claim 1, wherein said input data is stored in a storage device and is provided to the computer by loading from the storage device into the computer memory.

9. A process according to claim 1, wherein said input data is provided by scanning a surface of a three-dimensional model and fed to the computer.

10. A process according to claim 1, wherein said modification includes adaptation, alteration, or extension of said input three-dimensional body, or altering the location of the preparation line.

11. A process according to claim 1, further comprising generating on the display of the computer through the computer-aided design program a movable horizontal line to set or alter the location of the preparation line on the representation of the input three-dimensional body.

12. A process according to claim 1, further comprising the step of:

automatically generating modifications in the input data based upon comparisons with the mathematical models.

13. A process according to claim 1, further comprising the step of:

generating macro models representing basic functions performed in copying and production, the functions including creation of a base surface, consideration of tooth type, formulation of vertical and circular sections or contours of a tooth or selected variant, altering the height of a tooth in various vertical sections, bulging of inner and outer sides of a tooth thickness of a tooth sleeve.

14. A process according to claim 1, further comprising the step of:

generating through the computer-aided design program a recess in the representation of the vertical section of the input three-dimensional body at a location below the preparation line.

15. A process according to claim 1, further comprising the step of:

generating through the computer-aided design program a representation on the display of the computer of at least a portion of the preparation line.

16. A process according to claim 1, further comprising the step of:

generating through the computer-aided design program a representation of a three-dimensional body resulting from a merging of the input three-dimensional body and of the mathematical models.

17. A process according to claim 1, wherein said manufactured three-dimensional body is a tooth shell and said process further comprises the step of:

modifying through the computer-aided design program an angle of intersection between the tooth shell and the preparation line of a three-dimensional body that the shell will be attached on.

18. An apparatus for generating data for manufacturing a three-dimensional body, said device comprising:
  a computer including a processor, memory, an input device, and an output device;
  means for generating input data for said computer, said data representing a three-dimensional body model;
  means for storing said input data in said computer;
  means for generating, first signals to form, based on said input data, a plurality of surfaces representing said three-dimensional body model, wherein each surface comprises a contour of a vertical section extending through a central axis of said three-dimensional body model;
  means responsive to activation of said input device for locating a preparation line on said contour of said three-dimensional body;
  means responsive to activation of said input device for generating second signals to modify contours of vertical sections in accordance with said desired three-dimensional body; and
  means responsive to activation of said input device for generating third signals to store output data which denotes modifications of said contours in response to said second signals, said output data being transmittable from said computer to a manufacturing facility.

19. An apparatus according to claim 18, wherein said means for generating input data comprises a scanning device including means interacting with a surface of a three-dimensional body model for scanning a surface of the three-dimensional body.

20. An apparatus according to claim 19, further comprising a probe that interacts with the surface of the body.

21. A process for generating data for manufacturing a three-dimensional body utilizing a computer-aided design program, said process comprising the steps of:
  providing mathematical models corresponding to reference three-dimensional bodies, said mathematical models being stored in a memory of a computer;
  generating macro models representing standard copying and production functions including formation of a base of a three-dimensional body and altering width and height of a three-dimensional body;
  generating through the computer-aided design program a mathematical model by merging selected ones of the macro models with features of the mathematical models corresponding to reference three-dimensional bodies stored in the memory of the computer;
  providing to the computer input data representing an input three-dimensional body;
  generating through the computer-aided design program a representation the input data on a display of the computer, the representation comprising at least a portion of a contour of a vertical section extending through a central axis of the input three-dimensional body;
  determining a location of a preparation line on the representation of the input three-dimensional body for manufacturing the manufactured three-dimensional body;
  generating through the computer-aided design program a representation comprising at least a portion of a contour of a vertical section extending through a central axis of the one of the mathematical models on the display of the computer superimposed on the representation of the input data;
  generating through the computer-aided design program a representation comprising at least a portion of a contour of a vertical section extending through a central axis of the merged macro models and mathematical models on the display of the computer superimposed on the representation of the input data;
  generating through the computer-aided design program based upon a comparison of the representation of the input three-dimensional body with the representation of the merged macro models and mathematical models a modification of the input data on the display of the computer utilizing an input device of the computer; and
  generating through the computer-aided design program the output data representing the modified input three-dimensional body, the output data being transmittable from the computer for manufacturing the three-dimensional body.

22. The process according to claim 21, wherein the input three-dimensional body and manufactured three-dimensional bodies are teeth and the macro models utilize rules/mathematics linked to at least one basic form of tooth, the creation of a base type, tooth type, formulation of vertical and circular sections of a respective body variant/tooth, alteration of the height of the tooth in various vertical sections, bulging of the inner and outer sides of the tooth and thickness of a utilized tooth sleeve.

23. A process for generating data for manufacturing a three-dimensional body utilizing a computer-aided design program, said process comprising the steps of:
  providing mathematical models corresponding to reference three-dimensional bodies, said mathematical models being stored in a memory of a computer;
  providing to the computer input data representing an input three-dimensional body;
  generating through the computer-aided design program a representation the input data on a display of the computer, the representation comprising at least a portion of a contour of a vertical section extending through a central axis of the input three-dimensional body;
  determining a location of a preparation line on the representation of the input three-dimensional body for manufacturing the manufactured three-dimensional body;
  generating through the computer-aided design program a representation comprising at least a portion of a contour of a vertical section extending through a central axis of the one of the mathematical models on the display of the computer superimposed on the representation of the input data;
  generating through the computer-aided design program based upon a comparison of the representation of the input three-dimensional body with the representation of the mathematical model a modification of the input data on the display of the computer utilizing an input device of the computer;
  generating through the computer-aided design program upon activation of the input device signals to represent a displaceable unit, which, based upon the signals is controllable in the vertical direction of the vertical sections, wherein, upon displacement of the unit to a part of the respective vertical section representing the preparation line of the input three-dimensional body, the computer-aided design program generates through the computer and presents on the display a line represented by dots, the line representing the preparation line of the three-dimensional body to be manufactured when applied to a flat surface, and wherein data relating to the preparation line representation forms part of the output data; and generating through the computer-aided design program the output data representing the modified input three-dimensional body, the output data being transmittable from the computer for manufacturing the three-dimensional body.

24. A process for generating data for manufacturing a three-dimensional body utilizing a computer-aided design program, said process comprising the steps of:

providing mathematical models corresponding to reference three-dimensional bodies representing different types of teeth, said mathematical models being stored in a memory of a computer;

forming of a library for storing data files attributable to various basic types of teeth, and other variables including at least one of strength and facade material;

providing to the computer input data representing an input three-dimensional body;

generating through the computer-aided design program a representation the input data on a display of the computer, the representation comprising at least a portion of a contour of a vertical section extending through a central axis of the input three-dimensional body;

determining a location of a preparation line on the representation of the input three-dimensional body for manufacturing the manufactured three-dimensional body;

generating through the computer-aided design program a representation comprising at least a portion of a contour of a vertical section extending through a central axis of the one of the mathematical models on the display of the computer superimposed on the representation of the input data;

generating through the computer-aided design program based upon a comparison of the representation of the input three-dimensional body with the representation of the mathematical model a modification of the input data on the display of the computer utilizing an input device of the computer; and generating through the computer-aided design program the output data representing the modified input three-dimensional body, the output data being transmittable from the computer for manufacturing the three-dimensional body.

25. The process according to claim 24, further comprising continuously feeding data into the library files and utilizing the data in the creation of subsequent simulations and body variant formations.

26. The process according to claim 25, further comprising activating comparison-making members to conduct comparisons between a body variant under formation and previously formed body variants.

27. The process according to claim 24, wherein the library is formed using a self-teaching function, and wherein an optimal shape for a tooth type is based upon a total number of body variants created in the computer and possibly upon experience-based information.

28. The process according to claim 24, further comprising generating through the computer program signals for attaching to a respective vertical section an item of shell-thickness information, so that a shell is presented on the screen for a respective vertical section.

29. The process according to claim 24, further comprising generating through the computer program signals for influencing a connection angle of a respective vertical section, the connection angle is situated at the preparation line and relates to a shape of a connecting surface/connecting lip against a tooth remnant in question.

* * * * *

UNITED STATES PATENT AND TRADEMARK OFFICE
CERTIFICATE OF CORRECTION

PATENT NO. : 5,880,962
DATED : March 9, 1999
INVENTOR(S) : Matts Andersson et al.

It is certified that error appears in the above-identified patent and that said Letters Patent is hereby corrected as shown below:

On the title page, Item [54] and Col. 1, line 3,
    The title should read --...THEREFOR--, not "...THEREOF".

Signed and Sealed this

Twenty-ninth Day of June, 1999

Q. TODD DICKINSON

Attest:

Attesting Officer

Acting Commissioner of Patents and Trademarks